(12) United States Patent
Kotulla et al.

(10) Patent No.: US 7,389,133 B1
(45) Date of Patent: Jun. 17, 2008

(54) METHOD AND DEVICE FOR CONTINUOUS MONITORING OF THE CONCENTRATION OF AN ANALYTE

(75) Inventors: Reinhard Kotulla, Lambsheim (DE); Arnulf Staib, Heppenheim (DE); Ralph Gillen, Papenburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/870,606

(22) Filed: Oct. 11, 2007

Related U.S. Application Data

(63) Continuation of application No. 11/266,637, filed on Nov. 3, 2005, now abandoned, which is a continuation of application No. 10/945,798, filed on Sep. 21, 2004, now abandoned.

(30) Foreign Application Priority Data

Sep. 23, 2003 (DE) ................................ 103 43 863

(51) Int. Cl.
*A61B 5/05* (2006.01)
*A61B 5/00* (2006.01)
(52) U.S. Cl. ....................................... 600/345; 600/309
(58) Field of Classification Search ................ 600/300, 600/309, 346–366
See application file for complete search history.

(56) References Cited

U.S. PATENT DOCUMENTS

| | | | |
|---|---|---|---|
| 5,507,288 A | 4/1996 | Bocker et al. | |
| 5,921,937 A | 7/1999 | Davis et al. | |
| 6,272,480 B1 | 8/2001 | Tresp et al. | |
| 6,317,662 B1 | 11/2001 | Li et al. | |
| 6,519,705 B1 | 2/2003 | Leung | |
| 6,572,545 B2 * | 6/2003 | Knobbe et al. | ............. 600/365 |
| 6,575,905 B2 | 6/2003 | Knobbe et al. | |
| 6,584,335 B1 | 6/2003 | Haar et al. | |
| 6,740,518 B1 * | 5/2004 | Duong et al. | ............. 435/287.2 |
| 2003/0130616 A1 * | 7/2003 | Steil et al. | ................... 600/365 |

FOREIGN PATENT DOCUMENTS

| | | |
|---|---|---|
| EP | 0910023 A2 | 9/1998 |
| WO | 98/42249 A1 | 10/1998 |
| WO | 01/38948 A2 | 5/2001 |
| WO | 02/24065 A1 | 3/2002 |

OTHER PUBLICATIONS

S.D. Brown: "The Kalman Filter in Analytical Chemistry", Analytica Chimica Acta 181, (1986), pp. 1-26.
K. Gordon: "The multi-state Kalaman Filter in medical monitoring", Computer Methods and Programs in Biomedicine, 23 (1986), pp. 147-154.

(Continued)

*Primary Examiner*—Charles A. Marmor, II
*Assistant Examiner*—Navin Natnithithadha

(57) ABSTRACT

The disclosure generally relates to continuous monitoring of an analyte by determining its change over time in the living body of a human or animal. A measurement variable value correlating with the desired concentration of the analyte are measured as the measurement signal ($z_t$) and the change over time of the concentration is determined from the measurement signal as the useful signal ($y_t$) using a calibration. A filter algorithm is used to reduce errors of the useful signal, which result from noise contained in the measurement signal. The filter algorithm includes an operation in which the influence of an actual measurement value on the useful signal is weighted using a weighting factor (V).

9 Claims, 3 Drawing Sheets

OTHER PUBLICATIONS

K. Gordon, A.F.M. Smith: "Modeling and monitoring Biomedical Time Series", Journal of the American Statistical Association, 85 (1990), pp. 328-337.

XP-002310881—Kenneth A. Myers and Byron D. Tapley: "Adaptive Sequential Estimation with Unknown Noise Statistics", IEEE Transactions on Automatic Control, (Aug. 1976), pp. 520-523.

E. Knobble, W. Lim, B. Buckingham: Development of a Real Time Glucose Estimator Using Data Generated from the Medtronic Minimed® Continuous Glucose Monitoring Systems (CGMS), Department of Pediatric Endocrinology, Stanford University, (Feb. 14, 2003), pp. 16.

* cited by examiner

US 7,389,133 B1

METHOD AND DEVICE FOR CONTINUOUS MONITORING OF THE CONCENTRATION OF AN ANALYTE

REFERENCE TO RELATED APPLICATIONS

This application is a Continuation of U.S. patent application Ser. No. 11/266,637, filed Nov. 3, 2005 now abandoned which is a Continuation of U.S. patent application Ser. No. 10/945,798, filed Sep. 21, 2004 now abandoned, which claims priority to German Patent Application No. 10343863.7, filed Sep. 23, 2003, which are hereby incorporated by reference in their entirety.

TECHNICAL FIELD

The teachings of this application generally relate to a method and a device for continuous monitoring of the concentration of an analyte. In particular, the teachings relate to determining the analyte's change over time in the living body of a human or animal. The term "continuous monitoring" abbreviated (CM) is used hereafter for this purpose.

BACKGROUND

A CM method and device is described, for example, in U.S. Pat. No. 5,507,288.

Continuous monitoring of the concentration of glucose in the body of a patient can have great medicinal significance. Studies have led to the result that extremely grave long-term effects of diabetes mellitus (for example, blinding because of retinopathy) can be reduced if the change over time of the concentration of the glucose is continuously monitored in vivo. Continuous monitoring allows the required medication (insulin) to be dosed precisely at each point in time and to keep the blood sugar level always within narrow limits, similarly to a healthy person.

The present teachings relate in particular to CM of glucose. Further information can be taken from U.S. Pat. No. 5,507,288 and the literature cited therein. The content of this document is incorporated herein by reference.

The present teachings are, however, also suitable for other applications in which the change over time of an analyte in the living body (useful signal) is derived from a measurement signal, which comprises measurement values, measured at sequential points in time, of a measurement variable correlating with the concentration desired. The measurement signal may be measured invasively or non-invasively.

An invasive measurement method is described, for example, in U.S. Pat. No. 6,584,335.

Here a hollow needle carrying a thin optical fiber is stuck into the skin, light is irradiated under the skin surface through the optical fiber, and a modification of the light through interaction with interstitial liquid which surrounds the optical fiber is measured. In this case, the measurement signal comprises measurement values obtained from light which is returned through the optical fiber into a measurement device after the interaction. For example, the measurement signal may comprise spectra of the light which are measured at sequential points in time.

Another example of invasive measurement methods is the monitoring of concentrations by means of an electrochemical sensor which may be stuck into the skin. An electrical measurement variable, typically a current, is thus determined as the measurement variable which is correlated with the concentration of the analyte.

Different non-invasive methods are discussed in U.S. Pat. No. 5,507,288. These include spectroscopic methods in which light is irradiated directly (i.e., without injuring the skin) through the skin surface into the body and diffusely reflected light is analyzed. Methods of this type have achieved some importance for checking the change over time of oxygen saturation in the blood. For the analysis of glucose alternative methods are preferred, in which light is irradiated into the skin in a strongly localized manner (typically punctually) and the useful signal (course of the glucose concentration) is obtained from the spatial distribution of the secondary light coming out of the skin in the surroundings of the irradiation point. In this case the measurement signal is formed by the intensity profile, measured at sequential points in time, of the secondary light in the surroundings of the irradiation point.

A common feature of all methods of this type is that the change of the concentration over time (useful signal) is determined from the measurement values measured at sequential points in time (measurement signal) using a microprocessor system and a suitable algorithm. This analysis algorithm includes the following partial algorithms: a filter algorithm, by which errors of the useful signal resulting from signal noise contained in the measurement signal are reduced and a conversion algorithm, in which a functional relationship determined by calibration, which relationship describes the correlation between measurement signal and useful signal, is used.

Typically, these parts of the analysis algorithm are performed in the described sequence, i.e., first a filtered measurement signal is obtained from a raw measurement signal by filtering and the filtered signal is then converted into the useful signal. However, this sequence is not mandatory. The raw measurement signal can also be first converted into a raw useful signal and then filtered to obtain the final useful signal. The analysis algorithm may also include further steps in which intermediate variables are determined. It is only necessary in the scope of the present invention that the two partial algorithms a) and b) are performed as part of the analysis algorithm. The partial algorithms a) and b) may be inserted anywhere into the analysis algorithm and performed at any time.

The present teachings relate to cases in which time domain filter algorithms are used. Kalman filter algorithms are particularly common for this purpose. More detailed information on filter algorithms of this type is disclosed by the following literature citations, some of which also describe chemical and medical applications: S. D. Brown: The Kalman filter in analytical chemistry, Analytica Chimica Acta 181 (1986), 1-26; K. Gordon: The multi-state Kalman filter in medical monitoring, Computer Methods and Programs in Biomedicine 23 (1986), 147-154; K. Gordon, A. F. M. Smith: Modeling and monitoring biomedical time series, Journal of the American Statistical Association 85 (1990), 328-337; U.S. Pat. No. 5,921,937; EP 0 910 023 A2; WO 01/38948 A2; U.S. Pat. No. 6,317,662; and U.S. Pat. No 6,575,905 B2.

As noted, the filter algorithm is used for the purpose of removing noise signals which are contained in the raw measurement signal and would corrupt the useful signal. The goal of every filter algorithm is to eliminate this noise as completely as possible, but simultaneously avoid to disturb the measurement signal. This goal is especially difficult to achieve for in vivo monitoring of analytes, because the measurement signals are typically very weak and have strong noise components. Special problems arise because the measurement signal typically contains two types of noise, which differ significantly in regard to the requirements for the filter algorithm: measurement noise: such noise signal components follow a normal distribution having a constant standard deviation around the correct (physiological) measurement signal and non-physiological signal changes, which are caused, for example, by movements of the patient and changes of the coupling of a measurement sensor to the skin to which it is connected. They are typically neither distributed normally around the physiological measurement signal, nor is the standard deviation from the physiological measurement signal constant. For such noise components of the raw signal the term NNNC (non-normal, non-constant)-noise is used hereafter.

SUMMARY

Embodiments of the invention are based on the technical problem to achieve better precision of CM methods by improving the filtering of noise signals.

According to the embodiment of the invention, this is achieved by means of a filter algorithm which includes an operation in which the influence of an actual measurement value on the useful signal is weighted using a weighting factor ("controllable filter algorithm"), a signal variation parameter (related in each case to the actual point in time, i.e. time-dependent) is determined on the basis of signal variations detected during the continuous monitoring in close chronological connection with the measurement and the weighting factor is adapted dynamically as a function of the signal variation parameter determined for the point in time of the actual measurement.

Embodiments of the invention will be described in greater detail hereafter on the basis of the figures. The details shown therein and described in the following may be used individually or in combination to provide preferred embodiments of the present invention.

BRIEF DESCRIPTION OF THE DRAWINGS

The following detailed description of embodiments of the invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of embodiments of the invention.

DETAILED DESCRIPTION

The following description of embodiments is merely exemplary in nature and is in no way intended to limit the invention or its application or uses.

Figure 1:
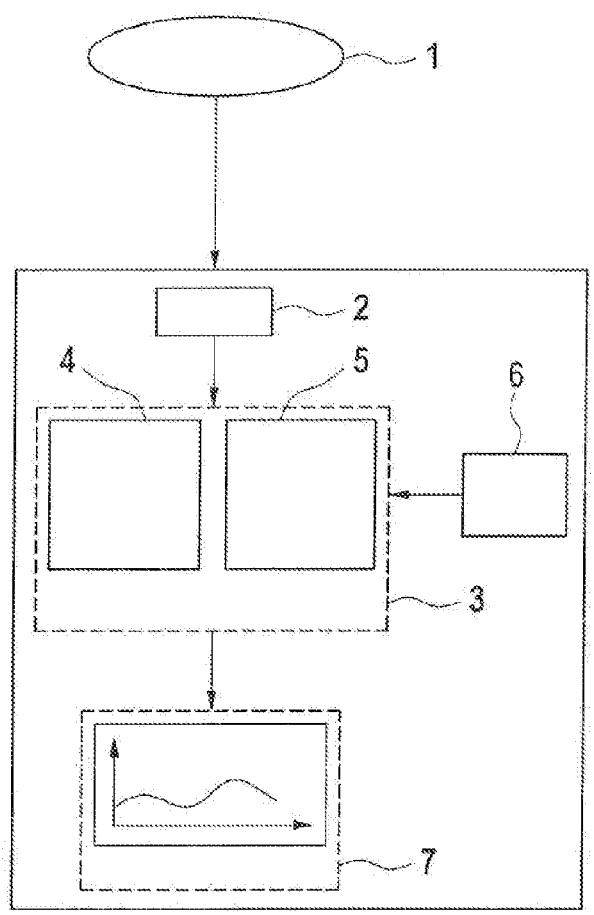
FIG. 1 shows a block diagram of a device according to embodiments of the invention.

The components of a CM device according to embodiments of the invention are shown in FIG. 1. As shown, a sensor 1 measures measurement values at sequential points in time. This measurement signal is transmitted—wirelessly, in the case shown—to a receiver 2, from which the measurement signal is further transmitted to an analysis unit 3, which contains a microprocessor 4 and a data memory 5. Data and commands may also be transmitted to the analysis unit 3 via an input unit 6. Results are outputted using an output unit 7, which may include a display and other typical output means. The data processing is performed digitally in the analysis unit 3 and corresponding converters for converting analog signals into digital signals are provided. Embodiments of the invention are suitable for a wide range of measurement techniques in which different measurement signals correlating to the desired useful signal are obtained.

Figure 2:
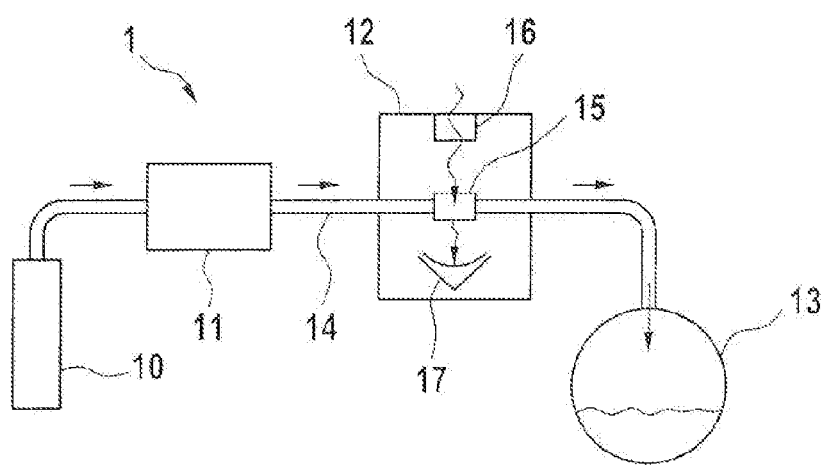
FIG. 2 shows a schematic diagram of a sensor suitable for embodiments of the invention.

FIG. 2 shows a sensor 1 in the form of a schematic diagram, in which an implantable catheter 10 is used in order to suction interstitial liquid from the subcutaneous fatty tissue by means of a pump 11. The tissue is then suctioned through a photometric measurement unit 12 into a waste container 13. The line 14 by which the interstitial liquid is transported contains a transparent measurement cell 15 which is arranged in the photometric measurement unit 12, into which primary light originating from a light emitter 16 is irradiated. The secondary light resulting after passing the measurement cell 15 is measured using a photodetector 17 and processed by means of measurement electronics (not shown) into a raw signal, which—as shown for exemplary purposes in FIG. 1—is transmitted to an analysis unit 3.

Figure 3:
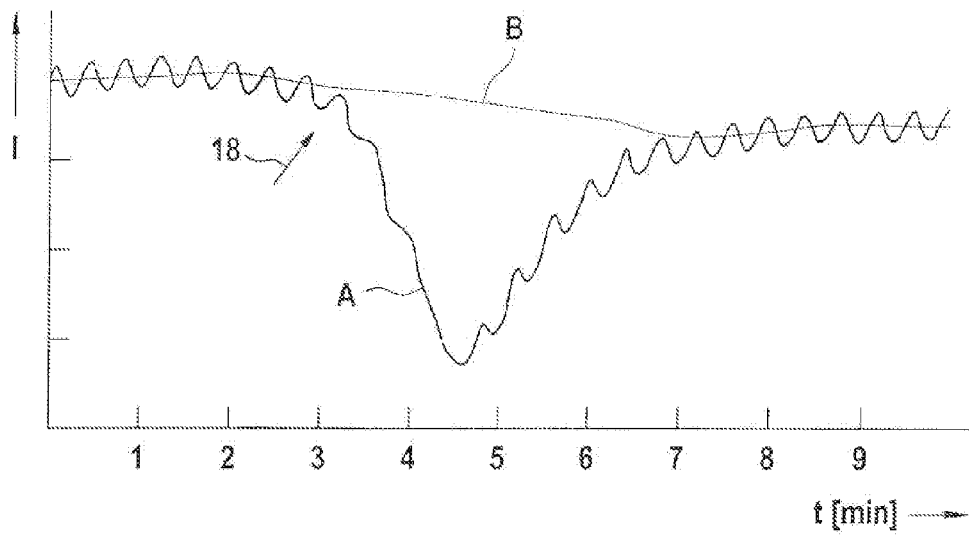
FIG. 3 shows a measurement signal of a sensor as shown in FIG. 2.

FIG. 3 shows the typical graph of a raw measurement signal as curve A obtained using a sensor as shown in FIG. 2. The intensity I of the secondary light is measured at a specific wavelength and plotted against the time t in minutes. FIG. 3 is based on a CM experiment in which the measurement values for curve A were measured at intervals of one second each.

Variations of the flow of the interstitial liquid from the body into the photometric measurement unit 12 lead to regular, relatively small signal variations, which are referred to as "fluidic modulation". After approximately three minutes, at the point in time identified with the arrow 18, an inhibition of the liquid flow occurred, which may be caused, for example, by movement of the patient or by the entrance of a cell particle into the catheter 10. This inhibition of the flow leads to a large drop of the raw measurement signal A. This is an example of the fact that not all noise signals are distributed normally, with essentially constant standard deviation, around the signal corresponding to the actual physiological measurement value. Rather also interfering contributions of the type shown here exist, for which these conditions do not apply (NNNC noise). Therefore, the signal requires filtering even in such cases in such a manner that a useful signal results which corresponds as closely as possible to the actual physiological concentration of the analyte. An example for such a useful signal is shown in FIG. 3 as thin line B.

The basis of a filter algorithm operating in the time domain, which embodiments of the invention relate, is a system model that describes the change over time of the variables of interest and their relationship to one another. The functional relationship which describes the development of the system from time t to time t+1 is as follows:

$$y_{t+1} = f_t(y_t, y_{t-1}, \ldots, u_t, u_{t-1}, \ldots)$$  Equation 1

Therein, $y_t$ and $u_t$ are vectors, which are referred to as state vectors and vectors of input variables, respectively. The state vector $y_t$ contains the variables of physiological interest and optionally check variables, which allow to check the measurement, as will be described in greater detail below. In the CM method, these include the desired analyte concentration, for example, the glucose concentration $g_t$ in the blood. The speed of change of the analyte concentration $g_t' = dg_t/dt$ is suitable as a check variable. The state variable $y_t$ may also contain model variables related to the measurement method. For example, in the case of a measurement result of the type shown in FIG. 3. It is advantageous to incorporate fluidic modulations into the system model. These modulations may be described using their time-dependent frequency $\omega_t$ and the amplitude $A_t$, which is also time-dependent. Therefore, four system variables result for the experiment described on the basis of FIGS. 2 and 3: $g_t$, $A_t$, $\omega_t$, $g_t'$.

Input variables which, in the field of automatic control, correspond to control variables and are therefore not measured themselves are entered into the vector $u_t$. In the case of glucose monitoring, for example, the administered insulin quantity given and the bread exchange units supplied are suitable input variables, because they both influence the glucose concentration in the blood. If these input variables are used, the vector $u_t$ has two elements: insulin dose and bread exchange units. A characteristic feature of input variables is that no prediction of their future values is necessary in the scope of the filter algorithm.

The mentioned variables of the state vector $y_t$ and the input vector $u_t$ are, of course, only to be understood as examples. Embodiments of the invention relate to greatly varying systems which require different system models. It is not necessary to use the models in a discrete form. The continuous form with the corresponding differential equations may also be used.

A feature of filter algorithms in the time domain is that they include an alternating sequence of predictions and corrections. A prediction of the system state ("predictor step") is followed by a subsequent correction of this prediction on the basis of a further measurement value ("corrector step").

In a predictor step, the actual value of the state variable $y_t$ at the point in time t is predicted using the following system equation:

$$\hat{y}_t = f_{t-1}(y_{t-1}, y_{t-2}, \ldots; u_{t-1}, u_{t-2}, \ldots) + w_{t-1} \quad \text{Equation 2}$$

In this equation, $\hat{y}_t$ identifies the value of the state vector at the point in time t which is estimated (predicted) using the data of the previous point in time (t−1); $W_t$ identifies a system error vector.

In the case of a recursive filter algorithm, the calculation of each predictor step is not performed by taking all preceding points in time (t−1, t−2, t−3, ...) into consideration, but rather by using a weighted sum of smoothed signal values. In the example of a linear Kalman algorithm, the corresponding equation may be written as follows:

$$\hat{y}_t = A_{t-1} y_{t-1} + B u_{t-1} + w_{t-1} \quad \text{Equation 2a}$$

In this equation 2a, $A_t$ is the system matrix and B is the input matrix. In the general (non-linear) case, $f_t$ is to be preset or is to be calculated from data determined up to this point.

In the corrector step, the prediction is corrected on the basis of an actual measurement value according to the following equation.

$$y_t = \alpha_t \hat{y}_t + \beta_t \Delta_t \quad \text{Equation 3}$$

In this equation, $\Delta_t$ is a variable which represents a measure of the deviation of an actual measurement value $z_t$ from the predicted value and is referred to as the "innovation".

$$\Delta_t = z_t - h(\hat{y}_t) \quad \text{Equation 4}$$

Further it is taken into consideration that typically the system variables cannot be observed directly. The linkage between the measurement values and the state variables is provided by means of a measurement model (measurement function $h_t$) according to:

$$z_t = h_t(y_t) + v_t \quad \text{Equation 5}$$

The noise of the measurement values is taken into consideration by $v_t$.

In the case of a linear Kalman algorithm (cf. equation 2a), the measurement equation is $$z_t = H_t y_t + V_t, \quad \text{Equation 5a}$$

$H_t$ referring to the measurement matrix.

For example, in the continuous monitoring of glucose using an electrochemical sensor, a current i is measured which is correlated with the glucose concentration $g_t$. In that example, $h_t$ describes the correlation of the state variable $g_t$ with the measurement variable i (current), which is an element of the vector $z_t$.

In the given example of photometric glucose detection using filter-assisted compensation of the fluidic modulation, a non-linear measurement model is used which links the photometric measurement signal $z_t$ to the system variables of glucose concentration $g_t$, amplitude $A_t$, and frequency $\omega_t$ of the fluidic modulation: $z_t = g_t + A_t \cdot \sin(\omega_t \cdot t)$.

According to equation (3), the influence of the actual measurement value (contained in the innovation $\Delta_t$) on the filtered useful signal value $y_t$ is weighted by the factors $\alpha_t$ and $\beta_t$. The described algorithm is therefore a controllable filter algorithm.

In the case of a Kalman filter, $\alpha_t = 1$ for every point in time and $\beta_t = K_t$. $K_t$ refers to the Kalman gain. Accordingly, the corrector equation is as follows:

$$y_t = \hat{y}_t + K_t \Delta_t \quad \text{Equation 3a}$$

Further details regarding the Kalman gain $K_t$ and more detailed information on the algorithm may be taken from the relevant literature, as cited above. Expressed descriptively, the Kalman gain is a measure of the weight given to additional measurement values. The Kalman gain is calculated anew in every iteration step of the filter algorithm according to an equation which may be written in simplified form (for the linear case) as follows:

$$K_t = P_t \cdot H_t \cdot (P_t \cdot H_t + V)^{-1} \quad \text{Equation 6}$$

Here, $P_t$ designates the Kalman error covariance matrix. V designates the measurement error covariance matrix in the conventional Kalman algorithm.

Equation (6) shows that the elements of $K_t$ may assume only values between 0 and 1. If the assumed measurement error V is relatively large in relation to the Kalman error covariance $P_t$, $K_t$ is small, i.e., the particular actual measurement value is given relatively little weight. In contrast, if V is small in relation to $P_t$ (multiplied by $H_t$), a strong correction occurs due to the actual measurement value.

Figure 4:
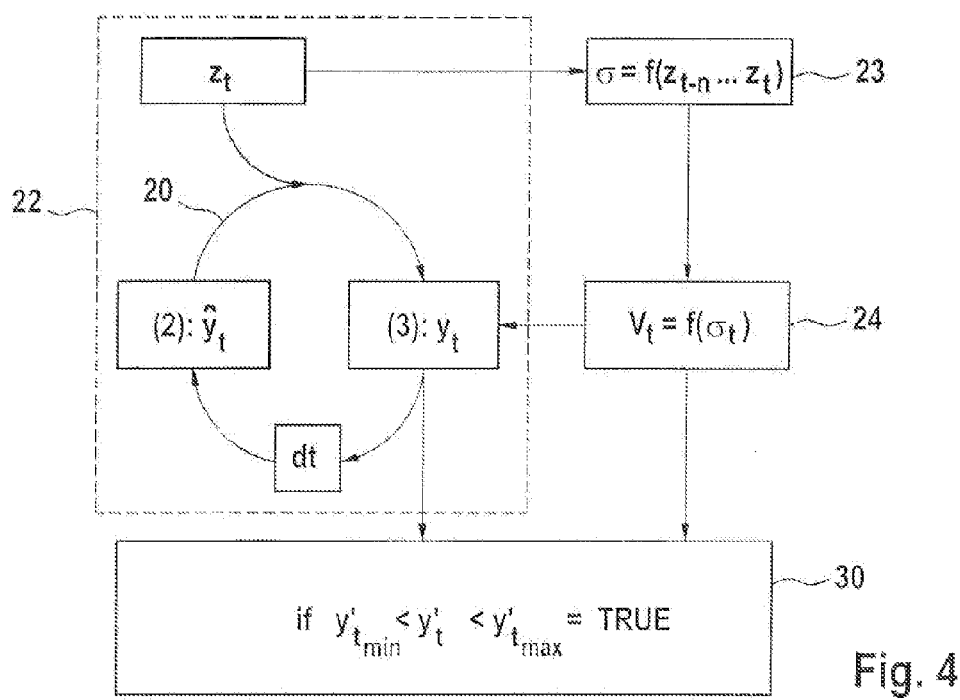
FIG. 4 shows a symbolic flowchart to explain the algorithm used in embodiments of the invention.

FIG. 4 shows in graphic form the iteration loop 20 which is the basis of the filter procedure. Alternately a corrector step which takes an actual measurement value $z_t$ into consideration, and, after a time step dt, a predictor step for a new point in time are performed. For example, the corrector step may be calculated according to equation (3) or (3a) and the predictor step according to equation (2) or (2a). This part of the algorithm is referred to as the filter core 22. As explained, it may be implemented in different ways, as long as it is an algorithm operating in the time domain and it includes an operation in which the influence of an actual measurement value $z_t$ on the filter useful signal $y_t$ is weighted using a weighting factor $\alpha_t$, $\beta_t$, or $K_t$, respectively.

An improvement of the filtering is achieved on the basis of signal variations detected in close chronological relationship with the measurement of the actual measurement value $z_t$, a signal variation parameter, designated here as $\sigma_t$, is determined and the weighting of the influence of the actual measurement value $z_t$ is dynamically adapted in the context of the corrector step as a function of $\sigma_t$. This is shown in graphic form in FIG. 4: box 23 symbolizes the calculation of the variation parameter $\sigma_t$ as a function of the measurement signal in a preceding period of time (measurement values $z_{t-n} \ldots z_t$). Box 24 symbolizes the calculation of the weighting factor taken into consideration in the corrector step (here, for example, the measurement error covariance V, which influences the Kalman gain), as a function of the signal variation parameter $\sigma_t$. The weighting factor is a time-dependent (dynamically adapted) variable (in this case $V_t$).

The present invention does not have the goal of weighting different filter types—like a filter bank—by applying weighting factors. For this purpose, a series of system models analogous to equation (2) would have to be defined, one model for each filter of the filter bank. This is not necessary in the present invention, whereby the method is less complex.

No precise mathematical rules may be specified for the functional relationships used in steps 23 and 24, because they must be tailored to each individual case. However, the following general rules apply.

The signal variation parameter is determined as a function of measurement values which have a close chronological relationship to the particular actual measurement value. In this way, the speed of the filter is sufficient. The determination of the signal variation parameter is preferably based on measurement values which were measured less than 30 minutes, preferably less than 15 minutes, and especially preferably less than 5 minutes before the measurement of the actual measurement value. At the least, measurement values from the periods of time should be included in the algorithm for determining the signal variation parameter.

Independently of the equations used in a particular case, the principle applies that with decreasing signal quality (i.e., for example, increase of the standard deviation of the measurement signal), the signal variation parameter and therefore the weighting factor (or possibly the weighting factors) are changed in such a direction that the influence of the currently actual measurement value is reduced.

The standard deviation, which may be calculated as follows, is suitable as the signal variation parameter, for example.

If one assumes that the determination of the standard deviation is based on the actual measurement values z and four preceding measurement values $z_1$ to $z_4$, and if the difference between z and the preceding values is referred to as $\delta z$ ($\delta z_n = z - z_n$), the average value $\varepsilon$ is calculated as $$\varepsilon = \frac{1}{4}(\delta z_1 + \delta z_2 + \delta z_3 + \delta z_4) \qquad \text{Equation 7}$$

and the slope $\varphi$ of a linear smoothing function is calculated as $$\varphi = \frac{3(\delta z_1 - \delta z_4) + \delta z_2 - \delta z_3}{10} \qquad \text{Equation 8}$$

The standard deviation of the four values of the differences $\delta 1$, $\delta 2$, $\delta 3$, $\delta 4$ in relation to the linear smoothing function is $$\sigma_t = \left[\frac{1}{3}(\delta z_1 - (\varepsilon + 1.5\varphi))^2 + \frac{1}{3}(\delta z_2 - (\varepsilon + 0.5\varphi))^2 + \frac{1}{3}(\delta z_3 - (\varepsilon - 0.5\varphi))^2 + \frac{1}{3}(\delta z_4 - (\varepsilon - 1.5\varphi))^2\right]^{\frac{1}{2}} \qquad \text{Equation 9}$$

On the basis of this standard deviation $\sigma_t$, a dynamic (time-dependent) measurement error covariance $V_t$, which is included in a filter core with the Kalman algorithm, may be calculated, for example, according to $$V_t = (\sigma_0 + \sigma_t)^\gamma \qquad \text{Equation 10}$$

In this case, $\sigma_0$ and $\gamma$ are constant parameters which characterize the filter, and which may be set to tailor the chronological behavior of the filter, in particular its adaptivity, to a particular application.

In the example of a controllable recursive filter, the weighting factors $\alpha_t$, $\beta_t$ from equation (3) are a function of the signal variation parameter in such a manner that with increasing $\sigma_t$, factor $\alpha_t$ becomes larger and factor $\beta_t$ becomes smaller.

As already explained, equations (7) through (10) only represent one of numerous possibilities for calculating a signal variation parameter and, based thereon, a weighting factor for a controllable filter algorithm in the time domain. The standard deviation, which may, of course, be calculated using a varying number of measurement values, can be replaced by variables which represent a measure for the signal variations in a period of time preceding an actual measurement value. The term "signal variation parameter" is used generally to identify a mathematical variable which fulfills these requirements.

Figure 5:
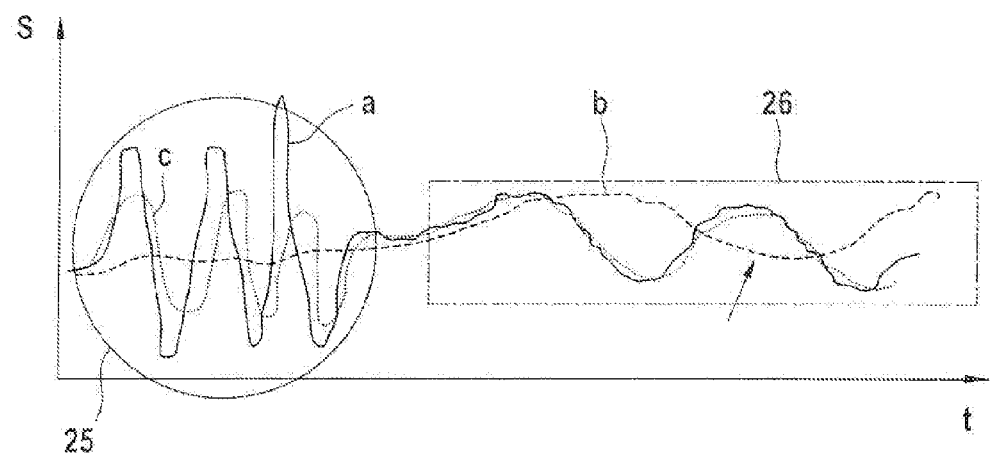
FIG. 5 shows a graphic illustration of typical signal curves to explain problems solved by embodiments of the invention.

Three typical graphs of a signal S are plotted against time t in FIG. 5, specifically:
- as a solid line, a raw signal with strong non-physiological variations in the time period enclosed by circle 25 and oscillates significantly less in the time period enclosed by rectangle 26, these variations being essentially physiological;
- as a dashed line, a useful signal, which was obtained from the raw signal a) using a Kalman filter, whose measurement error covariance was set corresponding to the variation of the raw signal in the circle 25; and,
- as a dotted line, a useful signal which was obtained from the raw signal a) using a Kalman filter, whose measurement error covariance was set corresponding to the graph of the raw signal in the rectangle 26.

Evidently, in the case of curve b the strong variations are filtered well within the circle 25, but in the rectangle 26, the signal b reflects the physiological variations of the raw signal insufficiently. The useful signal c, in contrast, follows the physiological variations in the region 26 well, while the filtering of the non-physiological variations in the region 25 is insufficient. The conventional Kalman filter algorithm therefore allows no setting which leads to optimal filtering for the different conditions shown. In contrast, the teachings do not even require knowledge of the maximum variations of measurement values. The filter algorithm adapts itself automatically to the changes in the signal course and provides a filtered signal which corresponds to the curve b in the circle 25 and to the curve c in the rectangle 26.

Figure 6:
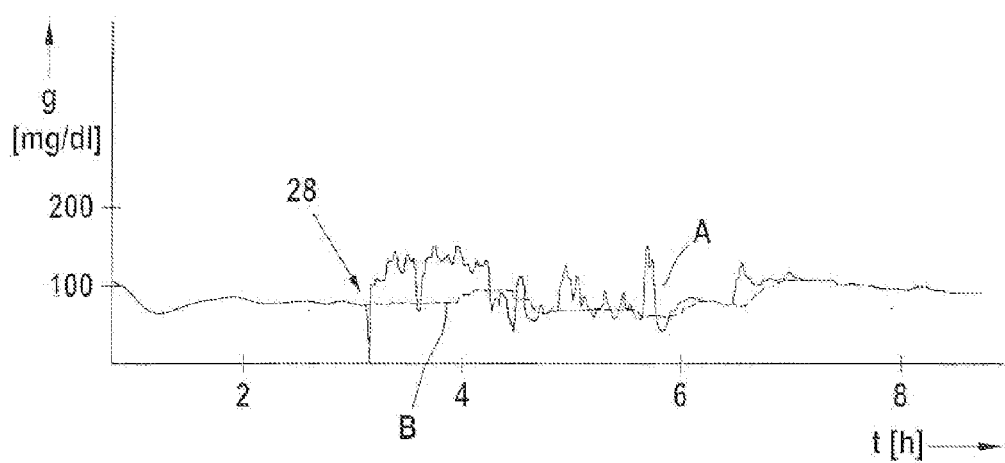
FIG. 6 shows a graphic illustration of experimentally obtained measurement results.

FIG. 6 shows corresponding experimental results from a CM experiment for glucose monitoring. A useful signal resulting from conventional filtering is shown as the solid curve A (glucose concentration in mg/dl) over the time in hours. The dashed curve B is the useful signal filtered according to the present invention. At the point in time marked with the arrow 28, the patient begins to move which interferes with the signal curve. Although there is very little variation of the free analyte concentration, the noise caused by the movement (NNNC noise) cannot be filtered out by the conventional filter. In contrast, using the filtering according to the present invention, a useful signal is obtained which approximates the physiological glucose curve very closely.

Significant additional reliability may be achieved if the filtering extends not only to the desired analyte concentration, but rather additionally to at least one further variable, which is designated "check variable". This may be a variable derived from the analyte concentration, in particular its first, second, or higher derivative versus time. Alternatively, an additional measurement variable, such as the flow of the interstitial liquid at the sensor shown in FIG. 2, can be used.

This check variable may, as explained above (for $g_t'$, $A_t$, and $\omega_t$), be included in the filter algorithm as a system variable. The filtering then also extends to the check variable, for which corresponding reliable smoothed useful signal values are available as the result of the filtering. These may then be compared to threshold values, in order to perform plausibility checks, for example. In the case of the glucose concentration, for example, it is known that the glucose concentration physiologically does not change by more than 3 mg/dl/min under normal conditions. A higher filtered value of the time derivative $g_t'$ is a sign of a malfunction. Therefore the query 30 shown in FIG. 4 compares the value of $y_t'$ to a minimum value and a maximum value. The value $y_t$ is only accepted as correct if $y_t'$ lies within these limits. Such a comparison would not be possible using the useful signal A in FIG. 6, because the insufficiently filtered non-physiological variations would lead to false alarms.

In order that embodiments of the invention may be more readily understood, reference is made to the following examples, which are intended to illustrate the invention, but not limit the scope thereof.

It is noted that terms like "preferably", "commonly", and "typically" are not utilized herein to limit the cope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purpose of describing and defining embodiments of the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

As any person skilled in the art will recognize from the previous description and from the figures and claims, modifications and changes can be made to embodiments of the invention without departing from the scope of the invention as defined in the following claims.

What is claimed is:

1. A method for continuous monitoring concentration of an analyte by determining the analyte's change over time in the living body of a human or animal, the method comprising:

measuring at sequential points in time, measurement values of a measurement variable correlating with a desired concentration of the analyte;

measuring the measurement variable as a measurement signal $(z_t)$;

determining the change over time of the concentration of the analyte from the measurement signal as a useful signal $(y_t)$ by means of a calibration;

providing a filter algorithm in the time domain for determination of the useful signal $(y_t)$ from the measurement signal $(z_t)$, wherein the filter algorithm reduces errors of the useful signal resulting from noise contained in the measurement signal, wherein the filter algorithm includes an operation in which the influence of an actual measurement value on the useful signal is weighted by means of a weighting factor (V);

determining a time dependent signal variation parameter $(\sigma_t)$ related to an actual point of time on the basis of signal variations detected in close chronological relation to the measurement of the actual measurement value;

wherein the time dependent signal variation parameter being a measure for signal variations for a period of time preceding an actual measurement value and being determined on the basis of measurement values including values which were measured less than 30 minutes before the measurement of the actual value; and adapting dynamically the weighting factor as a function of the signal variation parameter determined for the point in time of the actual measurement, the weighting factor being changed in such a direction that the influence of the actual measurement value is reduced with increasing standard deviation of the measurement signal.

2. The method according to claim 1, wherein measurement values, which are measured less than 15 minutes before the measurement of the actual measurement value, are used in the determination of the signal variations.

3. The method according to claim 1, wherein measurement values, which are measured less than 5 minutes before the measurement of the actual measurement value, are used in the determination of the signal variations.

4. The method according to claim 1, wherein the filter algorithm is a recursive filter algorithm.

5. The method according to claim 4, wherein the filter algorithm is a Kalman filter algorithm.

6. The method according to claim 5, characterized in that the filter algorithm is a linear Kalman filter algorithm.

7. The method according to claim 1, wherein the variables of a system model upon which the filter algorithm is based comprise a check variable.

8. The method according to claim 7, wherein the check variable is a time derivative, wherein the time derivative is the first time derivative of the analyte concentration.

9. A device for continuous monitoring of a concentration of an analyte by determining the analyte's change over time in the living body of a human or animal, the device comprising:
- a measurement unit, by which measurement values of a measurement variable correlating with the desired concentration are measured as the measurement signal ($z_t$) at a sequential points in time;
- an analysis unit, by which the change over time of the concentration is determined by means of a calibration as a useful signal ($y_t$) from the measurement signal, and
- a filter algorithm in the time domain for determination of the useful signal ($y_t$) from the measurement signal ($z_t$) to reduce errors of the useful signal, which result from noise contained in the measurement signal;

wherein the filter algorithm includes operation, in which the influence of an actual measurement value on the useful signal is weighted using a weighting factor (V), such that a time dependent signal variation parameter ($\sigma_t$) is determined on the basis of signal variations detected in close chronological relationship with the measurement of the actual measurement value, wherein the time dependent signal variation parameter being a measure for signal variations for a period of time preceding an actual measurement value and being determined on the basis of measurement values including values which were measured less than 30 minutes before the measurement of the actual value; and the weighting factor is dynamically adapted as a function of the signal variation parameter determined for the point in time of the actual measurement, the weighting factor being changed in such a direction that the influence of the actual measurement value is reduced with increasing standard deviation of the measurement signal.

* * * * *

UNITED STATES PATENT AND TRADEMARK OFFICE
CERTIFICATE OF CORRECTION

PATENT NO. : 7,389,133 B1  Page 1 of 1
APPLICATION NO. : 11/870606
DATED : June 17, 2008
INVENTOR(S) : Reinhard Kotulla, Arnulf Staib and Ralph Gillen It is certified that error appears in the above-identified patent and that said Letters Patent is hereby corrected as shown below:

In column 8, line 1, please change "Φ" to --φ--

Signed and Sealed this

Seventeenth Day of February, 2009

JOHN DOLL
*Acting Director of the United States Patent and Trademark Office*